US006187048B1

(12) United States Patent
Milner et al.

(10) Patent No.: US 6,187,048 B1
(45) Date of Patent: *Feb. 13, 2001

(54) INTERVERTEBRAL DISC IMPLANT

(75) Inventors: Richard Milner, Selby; Paul Arrowsmith, Hull; Edith Jane Millan, Micklefield, all of (GB)

(73) Assignee: Surgical Dynamics, Inc., Norwalk, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 9 days.

(21) Appl. No.: 08/971,582
(22) PCT Filed: May 23, 1995
(86) PCT No.: PCT/GB95/01166
  § 371 Date: Feb. 7, 1997
  § 102(e) Date: Feb. 7, 1997
(87) PCT Pub. No.: WO95/31946
  PCT Pub. Date: Nov. 30, 1995

Related U.S. Application Data

(63) Continuation of application No. 08/737,671, filed on Feb. 7, 1997, now abandoned.

(30) Foreign Application Priority Data

May 24, 1994 (GB) .................................................. 9410327
Oct. 7, 1994 (GB) .................................................. 9420290
Oct. 7, 1994 (GB) .................................................. 9420291

(51) Int. Cl.$^7$ ........................................................ A61F 2/44
(52) U.S. Cl. ...................................... 623/17.12; 623/17.16
(58) Field of Search .................................. 623/16, 17, 18, 623/17.12, 17.16; 606/60, 61

(56) References Cited

U.S. PATENT DOCUMENTS

| | | | |
|---|---|---|---|
| 4,904,260 | * 2/1990 | Ray et al. ................................ | 623/17 |
| 5,258,043 | * 11/1993 | Stone ...................................... | 623/17 |
| 5,314,478 | * 5/1994 | Oka et al. .............................. | 623/17 |
| 5,461,124 | * 10/1995 | Ritter et al. ........................... | 526/84 |
| 5,556,429 | * 9/1996 | Felt ........................................ | 623/18 |
| 5,562,736 | * 10/1996 | Ray et al. .............................. | 623/17 |
| 5,571,189 | * 11/1996 | Kuslich ................................... | 623/17 |

FOREIGN PATENT DOCUMENTS

| | | | |
|---|---|---|---|
| 0392734 | * 10/1990 | (EP) ....................................... | 623/17 |
| 9210982 | * 7/1992 | (WO) ...................................... | 623/17 |

\* cited by examiner

*Primary Examiner*—Michael J. Milano

(57) ABSTRACT

An implant for forming an intervertebral disc nucleus pulposus prosthesis includes a conformable material adapted to fill cavities within the disc and to at least partially polymerize in-situ to form a shaped, resiliently deformable prosthesis.

26 Claims, No Drawings

INTERVERTEBRAL DISC IMPLANT

This application is a continuation of application Ser. No. 08/737,671 filed Feb. 7, 1997 now abandoned.

BACKGROUND OF THE DISCLOSURE

The present invention relates to prosthetic devices and in particular to such devices which deform when in use (eg. when under compressive load). Here particularly the present invention relates to disc nucleus prostheses.

The intervertebral disc comprises three regions, the annulus fibrosus, the nucleus pulposus within the annulus fibrosus, and the cartilaginous end plates. Herniation of the disc may cause the nucleus pulposus to leak through a rupture point in the annulus fibrosus and bear against the ganglia of the spinal nerve, causing severe pain in the back as well as the legs. Surgical procedures to alleviate this condition include excision of the disc, chemo nucleolysis and spinal fusion. Another approach has been to replace the nucleus pulposus with a synthetic material. Thus in U.S. Pat. Nos. 5,047,055 and 5,192,326 it is proposed to replace the nucleus pulposus with a hydrogel in a hydrated form. The axial compression stresses acting upon an intervertebral disc which can vary between 0.15 MPa and 1.5 MPa depending upon the posture and activity involved. With highly hydrated material there is a propensity for the free water with hydrogel to be expelled.

In U.S. Pat. Nos. 4,772,287 and 4,904,206 it is, inter alia, proposed to at least partially replace the annulus pulposus with a prosthesis comprising two capsules arranged side-by-side, each filled with a therapeutic fluid. Similarly in European Patent No.480954 there is disclosed a balloon which is insertable into the cavity formed after removal of nucleus pulposus and which is fillable with fluid thereby to expand within the cavity. Such devices require a valve to prevent excess of the fluid where the disc is under an axial compression load, e.g. by bending.

In U.S. Pat. No. 3,875,595 there is disclosed a collapsible plastic bladder-like prosthesis of generally the same external form as the nucleus pulposus which is provided with a stem such that it can be filled with an unspecified liquid or plastic. The bladder also carries a stud for engagement within a recess formed in the cartilage end-plate or the over/underlying bone of the spinal column to retain the bladder in place. This disadvantage associated with such devices are the surgical procedure needed to form the recess sufficient to receive the stud and the need to prevent excess fluid when the disc is compressed.

The present invention seeks to avoid the disadvantages of the prior art proposals by the provision of a prosthesis which is simpler and cheaper to install and is not subject to mechanical failure.

SUMMARY

Accordingly, there is provided an implant for forming an intervertebral disc nucleus pulposus prosthesis comprising a conformable material adapted to fill cavities within the intervertebral disc and to be cured in-situ to form a shaped resiliently deformable prosthesis.

The invention further provides a method for replacing at least part of an intervertebral disc nucleus pulposus by implanting, within a cavity in the disc, an implant material in accordance with the invention and curing said material in-situ.

DESCRIPTION OF THE PREFERRED EMBODIMENTS

The term curing as used herein means any chemical reaction to form covalent or other bonds, for example hydrogen bonds.

The prosthesis may be used to replace or supplement body components which deform in the natural state. The prosthesis may thus be used for example, in breast implantation in cosmetic surgery, (such as in replacement of soft tissue for cosmetic purposes) in tissue expansion, in plastic surgery, etc.

Preferably, however the prosthesis is an intervertebral disc nucleus prosthesis.

The curable material desirably forms a solid or semi-solid elastomeric structure when cured and may be injected directly into the nucleus cavity. Alternatively a flexible cover or envelope may be used and can be provided so that it is impermeable to such toxic materials and they can therefore be maintained enclosed within the cover.

Desirably the curable material and the cured material are biocompatible, especially if the material is to be cured in-situ without a cover.

The curable material is flowable and is preferably in liquid form or in the form of a low viscosity gel (although it may be in the form of a particulate solid). This enables the implant material to flow easily so as to be able to conform to the desired shape before curing occurs.

The curable material may be, for example, a polyfunctional isocyanate based prepolymer so that water can be used to effect curing by causing the formation of urea linkages. The number of isocyanate groups available to form such linkages can be kept low if it is desired to minimise $CO_2$ evolution and exotherm.

Blocked isocyanate prepolymers which, on crosslinking with active prepolymer, can cure about or below body temperature may also be used. An example of this type of system is Desmocup II (polyurethane resin containing blocked isocyanate groups based on toluene diisocyanate and p-isononyl phenol) reacted with a polyfunctional amine terminated polymer such as polyalkylene oxide amine terminated polymer (eg. Jeffamine D2000 sold by Texaco Chemicals). The hydrophilicity of these systems may be varied by reaction of the blocked isocyanate resin with polyfunctional amine terminated polymers which contain a high proportion of ethylene oxide (eg. Jeffamine ED-600). Alternatively the blocked isocyanate polyurethane prepolymers may be prepared using polyols with high ethylene oxide content.

The curable implant materials may also include catalysts to promote or accelerate the curing reaction. Suitable catalysts for the isocyanate systems include tin catalysts such as Metatin 812ES.

Alternatively the material may comprise mixtures of poly(hydroxyalkyl(meth)acrylates) and poly(alkyl(meth)acrylates) crosslinked using polyfunctional (meth)acrylate monomers or oligomers, (eg. triethyleneglycol dimethacrylate. The reagent may be cured at low temperature (eg. 37° C. to ambient) by using a free radical initiator and an amine activator (eg. benzoyl peroxide and dimethyl p-toluidene). Preferably the alkyl groups contain from 1 to 4 carbon atoms.

The curable material may also consist of a mixture of tetra and trifunctional epoxy resin blend reacted with multifunctional amines and amino terminated elastomers such as an epoxy terminated silane and an amino terminated nitrile rubber. The material may comprise a monomer oligomer or polymer which contains ethylenic unsaturation. The ethylenic unsaturation may be acrylic or methacrylic unsaturation. Epoxy resins can also be added to the blocked isocyanate prepolymer (carbamic aryl ester capped urethane polymer—Desmocap II) polyfunctional amine system previously described for strengthening purposes.

Polymer complexes may also be used eg. complexes formed between the following polyanions, poly (sodium acrylate), poly (sodium vinyl sulphate) sodium poly phosphates, sodium polystyrene sulphonate and the following polycations: poly (N,N,N-trialkylammonioalkylacrylate), poly (N-alkylpyridinium) cation. There are several natural polymers which are capable of forming complexes. Anionic polymers include: sodium carboxymethyl cellulose, sodium cellulose sulphate, sodium alginate, sodium hyaluronate. Cationic polymers include: chitosan, quaternised chitosan, amino alkylated and subsequently quaternised cellulose, and poly-L-lysine.

Another alternative is to use siloxanes comprising functional groups which allow curing of the siloxanes with water to occur (eg. alkoxy, acyloxy, amido, oximo or amino groups). Acyloxy, acetoxy and alkoxy functionalities are most frequently employed. The number of siloxane groups can be determined such that the cured polymer is a resiliently deformable material.

Scavengers such as magnesium oxide may be advantageously employed if it is desired to reduce or eliminate any adverse effects of by-products of the curing reaction.

Inhibitors may also be included to control the exotherm generation in some systems such that the temperature of the implant material upon curing, does not increase much above that of body temperature. Suitable inhibitors can include p-methoxyphenol and hydroquinone.

The curable material need not be only a single component which cures with water since multi-component systems (for example mixtures of different polyisocyanates or of siloxanes as aforesaid) can be used.

In the case of single or multicomponent systems, the curing agent may be provided from the surrounding tissues after implantation (eg. where the curing agent is water or blood); mixed with the implanted curable material, or mixed outside the body and the resulting mixture implanted before the material is fully cured.

Suitable cover materials are conformable and aptly resistant to tearing or rupture when in use. The cover is preferably formed of a material which does not substantially bond to the curable material or to the cured material in order that such material is free to move or flow at least to a limited extent within the cover. The cover may be in the form of a membrane and maybe permeable to water. The degree of permeability may be chosen so as to control the role of diffusion of water and hence the rate of curing of the implant material.

Suitable materials for forming the cover include woven, braided and non-woven materials, which may be fibrous or non-fibrous. For fibrous materials the size of the fibres and the fibre density can be varied as appropriate to control porosity and/or mechanical strength. For non-fibrous materials (eg. plastics films) perforations of an appropriate size may be provided.

The cover may be a single layer or it may be multi-layer. It may be strengthened with reinforcement means, e.g., it may be sandwiched between two layers of resilient material, or be a fibre reinforced composite structure.

Suitable materials for forming the cover include polyethylenes (which may be ultra high molecular weight polyethylenes), polyester, polyurethane, polyesterurethane, polyester/polyol block copolymer, poly ethylene terepthalate, polytetrafluoro ethylene polyester, nylons, polysulphanes, cellulose materials, etc.

A preferred material for forming the cover is a water permeable polyurethane.

Water-permeable membrane materials said to be suitable for use in disc nucleus prostheses are disclosed in U.S. Pat. No. 5,192,326.

The cover is desirably provided with a sealable inlet eg. a valve by which curable material can be introduced to form the prosthesis. This may also function as an outlet for removing excess material, or a separate outlet may be provided.

The prosthesis of the present invention can be introduced into a disc nucleus space by any appropriate technique.

Preferably however the technique is one of minimal invasion whereby:

a) The material comprising the disc nucleus is removed using an appropriate surgical technique, e,g., curretage, suction, laser nucleotomy, chemonucleolysis, etc., and the space thus created is prepared to receive the prosthesis.

b) The curable material is introduced directly into the space formerly occupied by the nucleus pulposis through an aperture in the annulus fibrosus or by injection through the annulus. The curable material may be introduced under pressure in order to ensure conformation to the nucleus space and/or to increase the internal pressure of the disc and displace the vertebrae in a cephalad/cauded direction.

c) Once the nucleus space has been filled to a desired degree, the curable material is allowed to cure in situ.

In another embodiment, the curable material may be enclosed within a flexible container, in which case the technique may be:

a) The material comprising the disc nucleus is removed using an appropriate surgical technique, eg. curretage, suction, laser nucleotomy, chemonucleolysis, etc. and the space thus created, prepared to receive the prosthesis.

b) The cover is introduced into a disc nucleus space in the form of a flexible container (eg. a sac, which may be rolled up or otherwise stowed, if desired which is in an uninflated/only partially inflated state by means of an aperture in the annulus fibrosus (which may be made by a surgeon or which may have already occurred due to damage or ageing of the fibrosus).

c) Curable material is introduced into the flexible container so as to cause inflation thereof to a desired degree; and d) When the flexible container has been inflated to a desired degree the curable material is allowed to cure in situ.

The flexible container is desirably configured so as to adopt a shape generally conforming to that of the natural disc nucleus pulposis when inflated to a certain degree.

Aptly the curable material is introduced to the flexible container via injection through a valve. This can be done using a hypodermic syringe.

A probe may be introduced into the space formerly occupied by the nucleus pulposis or into the flexible container during filling thereof in order to determine the size of the prosthesis required for a given disc nucleus replacement. This can thus be used to determine when sufficient fluid is introduced into the flexible container. A suitable probe for this purpose is disclosed in WO 91/00713.

As an alternative to the probe, the disc nucleus space or a flexible cover introduced therein can be filled with a fluid which is detectable from outside of the body (eg. using by fluorimetry, x-rays or NMR techniques) whereby an observer can use a detector to see when the space has been filled to such a degree so that it adopts the desired shape. The amount of fluid required to do this can thus be determined. The fluid can then be removed and the space or a flexible container can be filled with the curable material to the pre-determined degree after washing or, if desired, the flexible container if used can be removed and replaced with a fresh flexible container, uncontaminated by said fluid, before filling the fresh flexible container to the pre-determined degree with available material. As a further alternative the detectable fluid may be present together with or as part of the curable material. In this instance it is desired that the detectable material does not adversely affect curing).

As another alternative, a probe incorporating a pressure transducer may be introduced into the nucleus space or the flexible container, either separately or incorporated into the hypodermic syringe. There exists in the scientific literature ample data on the pressures in the nucleus pulposis at rest and during activities. This data may be used to provide the surgeon with a range of pressure values to fill the space or flexible container.

The flexible container itself may comprise a detectable material detectable by using a detector outside of the body so that the outline of the flexible container can be seen. Therefore in this embodiment detectable fluid need not be introduced into the flexible container.

When the nucleus space or flexible container has been filled to a desired degree, any filling device or probe used may then be removed. If necessary damaged areas of the disc annulus fibrosis may be repaired or reinforced (eg. by suturing).

The prosthesis of the present invention may be provided with a circumferential reinforcement so that it can be used to replace the disc nucleus pulposis and the disc annulus fibrosus and can thus replace a complete inter-vertebral disc. A circumferential reinforcement in the form of a band of net material is disclosed in WO 93/16664.

In this embodiment it is desired that the prosthesis is mechanically secured in place by appropriate securing means (eg. screws, nails, sutures, adhesive etc.) in order to avoid the disc slipping out of the inter-vertebral space.

An in-situ curable system will now be illustrated in the following non-limiting examples of water curable silicone rubber in bags.

EXAMPLE 1

Commercially available silicone sealant, Silastic RTV 734 (Dow Corning) in admixtures with a magnesium oxide scavenger was placed in bags having dimensions of approximately 1 cm×2 cm and constructed from the following materials.

| Thickness | Material | Bag |
|---|---|---|
| 37 μm | Polyester/polyol block copolymer | (Hytrel G3548) |
| 25 μm | Polyester/polyol block copolymer | (Hytrel 8171) |
|  | Polyurethane | (Elastollan LP9109) |
|  | Polyester urethane | (Estane 58237) |
| 25 μm | Polyester urethane | (Estane 53815) |

Bags were prepared from each material by heat-sealing together 2 layers of the same film on three sides.

The bags were filled and then heat-sealed to form a "pillow". Two such filled bags were prepared from each film material. One bag of each film type was placed into water and the other was left overnight at room temperature in the air.

By morning all samples had become cured elastomers within a bag, demonstrating that the correct amount of water passes through the bag material to effect cure, even when immersed in water.

As the acetoxy silane reacts it generates acetic acid. However cells cannot tolerate a change in pH. The addition of magnesium oxide which effectively mops up the acetic acid as it is produced, is therefore an effective way of regulating the pH.

EXAMPLE 2

Silanol terminated poly dimethylsiloxane having a viscosity of about 1000 cS (10 g) was mixed with tetra ethoxy silane (Ig) and Metatin 812ES tin catalyst (0.3 ml). The mixture was of sufficiently low viscosity to be able to be delivered through a syringe. The mixture was poured into a bag formed by heat sealing two sheets of a 25 μm thick film of a polyester/polyol block polymer (Hytrel 8171). The bag was heat sealed and this bag was placed into a container of water. The mixture cured and became rubbery within the next 2 hours.

EXAMPLE 3

To a 25 ml beaker was added 2 g Craynor CN934 (difunctional aliphatic urethane acrylate oligomer—Cray Valley) and 0.15 g dimethyl-p-toluidene. The reagents were mixed until homogenous. To a second beaker was added 18 g 2-hydroxy ethylmethacrylate (2-HEMA) followed by 0.21 g benzoyl peroxide (70% benzoyl peroxide in water). The 2-HEMA solution was stirred whilst purging with nitrogen until all the benzoyl peroxide had dissolved then the solution was stirred by hand for approximately 1 minute then poured into a cylindrical mould (24 mm diameter, 23 mm height) and left to cure. A stiff material was obtained which became rubbery on hydration. Equilibrium water content was approximately 25% w/w.

EXAMPLE 4

To a 25 ml beaker was added 2 g Craynor CN904 and 0.075 g dimethyl-p-toluidene. The reagents were mixed until homogeneous. To a second beaker was added 6 g 2-HEMA, 6 g butyl acrylate and 0.105 g benzoyl peroxide (70% benzoyl peroxide in water). The 2-HEMA solution was stirred whilst purging with nitrogen until all the benzoyl peroxide had dissolved then the solution was added to the Craynor CN924 solution. The mixture was stirred by hand for approximately 1 minute then poured into a cylindrical mould. After 9 minutes the reagents began to cure. The reagents cured to give a rubbery material.

EXAMPLE 5

To a 25 ml beaker was added 2 g polybutadiene diacryl and 0.075 g dimethyl-p-toliduene. The reagents were mixed until homogeneous. To a second beaker was added 6 g 2-HEMA, 6 g butyl acrylate and 0.105 g benzoyl peroxide (70% benzoyl peroxide in water). The 2-HEMA solution was stirred whilst purging with nitrogen until all the benzoyl peroxide had dissolved then the solution was added to the Craynor CN934 solution. The mixture was stirred by hand for 9 minutes then poured into a mould. After a total of 25 minutes the reagents had cured to give a soft rubbery material.

EXAMPLE 6

To a 25 ml beaker was added 2 g Craynor CN924, 6 g 2-ethyl hexyl methacrylate and 0.075 g dimethyl-p-toliduene. The reagents were mixed until homogenous. To a second beaker was added 6 g 2-HEMA and 0.105 g benzoyl peroxide (70% benzoyl peroxide in water). The 2-HEMA solution was stirred whilst purging with nitrogen, until all the benzoyl peroxide had dissolved then the solution was added to the Craynor CN934 solution. The mixture was stirred by hand for approximately 2 minutes then poured into a bag prepared from Hytrel 8171, 25 micron film (having dimensions approximately 2.5 cm×3 cm) as described in Example 1. The filled bag was suspended from a Bull Dog clip in air. After 30 minutes the solution had cured to a rubber.

EXAMPLE 7

To a 50 ml beaker was added 15 g Democap 11 (polyurethane resin containing blocked isocyanate groups based on toluene diisocyanate and p-isononyl phenol) followed by 1.71 g Jeffamine D-400 (polyalylene oxide amine terminated difunctional polymer). The reagents were mixed by hand until homogeneous then poured into a cylindrical mould (24 mm diameter, 23 mm height) and left to cure over a weekend to cure at ambient temperature. A rubbery elastic gel was obtained.

EXAMPLE 8

To a 50 ml beaker was added 15 g Democap 11 followed by 8.57 g Jeffamine D-200 (polyalkylene oxide amine terminated difunctional polymer). The reagents were mixed by hand until homogeneous then poured into a cylindrical mould and left over a weekend to cure at ambient temperature. An extremely elastic gel was obtained.

EXAMPLE 9

Two implant materials were formulated employing the polysiloxane described in Example 1 and which 5% by weight magnesium oxide was added to scavenge acetic acid evolved during curing of the alhoxy silane groups. One of the resin formulations was further diluted with 40% silicone 0:1 200 (supplied by Dow Corning). The Shore A hardness of the undiluted formulation (I) was 22 wherein that of the diluted formulation (II) was C.

In a cadaver study, two hypodermic needles (12 gauge, 5 cm long) where inserted through the annulus into the nucleus of an intervertebral disc. Saline passed in through one needle and aspirated together with disc nucleus material for the other. Thereafter implant material was inserted into the nucleus through the needles. The implant material was allowed to cure whilst the region around the disc was kept moist by wrapping in gauze coated in physiological saline. The prostheses formed by cured implant material was exampled by sectioning the cadaver spines and it was found to have completely filled the nucleus cavity.

The spinal sections were also subjected to compression load testing and found to retain good integrity when subjected to a compression stress of about 1.16 MPa.

The implant materials of the present invention are therefore believed to possess good serviceable properties for use in forming prostheses.

What is claimed is:

1. An implant for forming an intervertebral disc nucleus pulposus prosthesis comprising a conformable material adapted to fill cavities within the disc and to at least partially polymerize in-situ to form a shaped, resiliently deformable prosthesis, said conformable material including at least approximately 85% by weight of a compound selected from the group consisting of polyhydroxyalkylmeth acrylates, polyalkylmethacrylates, and mixtures thereof.

2. An implant according to claim 1 wherein the conformable material is in the form of a fluid.

3. An implant according to claim 1 wherein at least part of the material is a functionalised prepolymer.

4. An implant according to claim 1 wherein at least part of the material is adapted to cured upon contact with water.

5. An implant according to claim 1 wherein at least part of the material is adapted to be cured by radiated energy.

6. An implant according to claim 5 wherein said radiated energy is thermal radiation or UV light radiation.

7. An implant according to claim 5 wherein said material further comprises an initiator.

8. An implant according to claim 3 wherein said material comprises a monomer oligomer or polymer comprising ethylenic unsaturation.

9. An implant according to claim 8 wherein said ethylenic unsaturation is acrylic or methacrylic unsaturation.

10. An implant according to claim 2 wherein the material is contained in a flexible envelope.

11. An implant according to claim 10 wherein the envelope is impervious to the material.

12. An implant according to claim 10 wherein the envelope contains means to allow ingress of a second material.

13. An implant according to claim 12 wherein the ingress means is sealable.

14. An implant according to claim 10 wherein the envelope is formed from water permeable polyurethane.

15. A method for implanting an intervertebral disc prosthesis into an intervertebral disc area defined between adjacent vertebrae comprising the steps of:

introducing a conformable material into the intervertebral disc area, the conformable material including at least approximately 85% by weight of a compound selected from the group consisting of polyhydroxyalkylmeth acrylates, polyalkylmethacrylates, and mixtures thereof, and being adapted to at least partially polymerize in situ; and curing the conformable material to at least cause partial polymerization thereof to thereby form a resiliently deformable intervertebral prosthesis.

16. The method of claim 15 wherein the step of curing includes subjecting the conformable material to an aqueous solution.

17. The method of claim 10 wherein the step of subjecting including introducing the aqueous solution into the intervertebral disc area to mix with the conformable material.

18. The method of claim 16 wherein the step of introducing includes permitting body fluids containing aqueous solution to enter the intervertebral disc area to mix with the conformable material.

19. The method of claim 16 wherein the step of subjecting includes mixing the aqueous solution with the conformable material, the step of mixing being performed prior to the step of introducing the conformable material into the intervertebral disc area.

20. The method of claim 16 further including the step of positioning a flexible container in the disc area and wherein the step of introducing includes directing the conformable material into the flexible container.

21. The method of claim 16 wherein the conformable material is an isocyanate or a siloxane.

22. The method of claim 15 wherein the step of curing includes subjecting the conformable material to radiated energy.

23. The method of claims 20 wherein the flexible container is permeable to the aqueous solution and wherein the step of subjecting includes permitting the aqueous solution to permeate the flexible container.

24. A method for implanting an intervertebral disc prosthesis into an intervertebral disc area defined between adjacent vertebrae, comprising the steps of:

introducing a conformable material into the intervertebral disc area, the conformable material adapted to at least partially polymerize in situ;

curing the conformable material to at least cause partial polymerization thereof to thereby form a resiliently deformable intervertebral prosthesis; and securing the prosthesis within the intervertebral disc area.

25. The method of claim 24 wherein the step of securing includes using mechanical securing means selected from the group consisting of screws, nails, sutures, and adhesives.

26. A method for implanting an intervertebral disc prosthesis into an intervertebral disc area defined between adjacent vertebrae, comprising the steps of:

positioning an impermeable container in the intervertebral disc area;

introducing a conformable material into the container, the conformable material adapted to at least partially polymerize in situ; and directing an aqueous solution into the container to at least cause partial polymerization of the conformable material to thereby form a resiliently deformable intervertebral prosthesis.

\* \* \* \* \*